(12) United States Patent
Kawazoe et al.

(10) Patent No.: US 9,344,199 B2
(45) Date of Patent: May 17, 2016

(54) OPTICAL RECEIVER AND LIGHT RECEIVING METHOD

(71) Applicant: FUJITSU OPTICAL COMPONENTS LIMITED, Kawasaki-shi, Kanagawa (JP)

(72) Inventors: Kenichi Kawazoe, Kurume (JP); Yuji Ishii, Fukuoka (JP); Tamotsu Akashi, Atsugi (JP); Koji Terada, Yamato (JP)

(73) Assignee: FUJITSU OPTICAL COMPONENTS LIMITED, Kawasaki (JP)

( * ) Notice: Subject to any disclaimer, the term of this patent is extended or adjusted under 35 U.S.C. 154(b) by 0 days.

(21) Appl. No.: 14/444,010

(22) Filed: Jul. 28, 2014

(65) Prior Publication Data

US 2014/0334831 A1 Nov. 13, 2014

Related U.S. Application Data

(63) Continuation of application No. PCT/JP2012/054459, filed on Feb. 23, 2012.

(51) Int. Cl.
*H04B 10/06* (2006.01)
*H04B 10/61* (2013.01)
*H04B 10/69* (2013.01)

(52) U.S. Cl.
CPC ............ *H04B 10/616* (2013.01); *H04B 10/693* (2013.01)

(58) Field of Classification Search
CPC .......................... H04B 10/616; H04B 10/693
USPC ........................................................ 398/210
See application file for complete search history.

(56) References Cited

U.S. PATENT DOCUMENTS

| 7,394,995 B2 * | 7/2008 | Audic ................. H04B 10/673 250/214 A |
| 7,482,958 B2 | 1/2009 | Tanaka et al. |
| 7,636,525 B1 * | 12/2009 | Bontu ................... H04B 10/60 398/208 |

(Continued)

FOREIGN PATENT DOCUMENTS

| JP | 2008-109562 | 5/2008 |
| JP | 2008-278249 | 11/2008 |

(Continued)

OTHER PUBLICATIONS

International Search Report mailed Mar. 27, 2012, in corresponding International Patent Application No. PCT/JP2012/054459.

*Primary Examiner* — Ken Vanderpuye
*Assistant Examiner* — Amritbir Sandhu
(74) *Attorney, Agent, or Firm* — Staas & Halsey LLP

(57) ABSTRACT

An optical receiver receives coherent light. The optical receiver includes an amplitude adjuster, a signal processor, and a controller. The amplitude adjuster adjusts amplitude of an input signal to output an analog signal. The signal processor receives a digital signal generated from the analog signal output from the amplitude adjuster, extracts clock components from the digital signal, and after establishing synchronization between the clock components and data components, extracts the data components from the digital signal to process the data components. The controller sets amplitude of the analog signal to first amplitude before establishment of synchronization by the digital signal, and changes the set amplitude to second amplitude that is smaller than the first amplitude after the establishment of synchronization.

5 Claims, 8 Drawing Sheets

(56) References Cited

U.S. PATENT DOCUMENTS

| | | | | |
|---|---|---|---|---|
| 7,734,193 B2* | 6/2010 | Day | ......................... | H03F 1/26 398/202 |
| 8,301,039 B2* | 10/2012 | Nishihara | ............... | H04B 10/61 375/229 |
| 8,326,145 B2* | 12/2012 | Takahara | ............. | H04B 10/695 398/202 |
| 8,526,102 B2 | 9/2013 | Inoue et al. | | |
| 8,942,334 B1* | 1/2015 | Zortea | .................. | H04L 7/0334 375/355 |
| 9,048,956 B2* | 6/2015 | Suzuki | ................. | H04B 10/612 |
| 2003/0222206 A1* | 12/2003 | Azary | .................. | G01C 15/006 250/214 AG |
| 2005/0196176 A1* | 9/2005 | Sun | .................... | H04B 10/6162 398/152 |
| 2005/0205759 A1* | 9/2005 | Wang | .................... | H04B 10/66 250/214.1 |
| 2005/0260000 A1* | 11/2005 | Domagala | ............ | H04B 10/299 398/188 |
| 2006/0110170 A1* | 5/2006 | Wang | ................... | H04B 10/695 398/208 |
| 2006/0256892 A1* | 11/2006 | Momtaz | ................ | H04L 25/061 375/317 |
| 2006/0285855 A1* | 12/2006 | Sun | ......................... | H04L 7/027 398/155 |
| 2007/0081827 A1* | 4/2007 | Ide | ......................... | H04B 10/66 398/209 |
| 2008/0267638 A1 | 10/2008 | Nakashima et al. | | |
| 2009/0245816 A1* | 10/2009 | Liu | ........................ | H04B 10/60 398/208 |
| 2010/0053397 A1* | 3/2010 | Yanai | ..................... | H04N 5/347 348/301 |
| 2010/0142971 A1* | 6/2010 | Chang | .................... | H04B 10/61 398/154 |
| 2011/0008046 A1* | 1/2011 | Sarashina | ............ | H04B 10/674 398/58 |
| 2011/0026940 A1 | 2/2011 | Komaki | | |
| 2012/0128377 A1* | 5/2012 | Hatae | ................... | H04B 10/616 398/208 |
| 2012/0237202 A1* | 9/2012 | Abe | ..................... | H04B 10/616 398/16 |
| 2014/0105616 A1* | 4/2014 | Yan | ....................... | H04L 7/0075 398/208 |
| 2014/0286651 A1* | 9/2014 | Takechi | ................ | H04B 10/614 398/208 |
| 2015/0171972 A1* | 6/2015 | Xie | ....................... | H04B 10/616 398/205 |

FOREIGN PATENT DOCUMENTS

| | | |
|---|---|---|
| JP | 2010-80665 | 4/2010 |
| JP | 2010-93656 | 4/2010 |
| JP | 2011-35551 | 2/2011 |
| WO | WO 2011/027895 A1 | 3/2011 |

\* cited by examiner

US 9,344,199 B2

OPTICAL RECEIVER AND LIGHT RECEIVING METHOD

CROSS-REFERENCE TO RELATED APPLICATION

This application is a continuation application of International Application PCT/JP2012/054459 filed on Feb. 23, 2012 and designating the U.S., the entire contents of which are incorporated herein by reference.

FIELD

The embodiments discussed herein are directed to an optical receiver and a light receiving method.

BACKGROUND

The rapid increase in the volume of communications traffic in optical transmission in recent years has created demand for technologies that allow high-quality data communications in high-speed transmission at about 100 Gbps that is largely affected by optical dispersion. One of the technologies is the digital coherent technology. An optical communication device to which the digital coherent technology is applied uses, for example, the dual polarization-quadrature phase shift keying (DP-QPSK) modulation scheme, for which standards are being developed by Optical Internetworking Forum (OIF). This optical communication device includes an optical transmitter that multiplexes a signal into an orthogonal polarization state, and an optical receiver that receives the multiplexed signal. The optical receiver includes a local light source such as a laser diode (LD) that emits light having substantially the same wavelength as that of received signal light. The optical receiver mixes the output light from the local light source with the received signal light to convert (perform coherent detection) the light into electrical signals of two (X, Y) polarizations each having IQ components. The optical receiver analog-to-digital (AD) converts the resulting signals, performs distortion correction and error correction, and outputs the signals to the outside of the optical receiver as a 100 Gbps information signal.

Patent Document 1: Japanese Laid-open Patent Publication No. 2010-93656
Patent Document 2: Japanese Laid-open Patent Publication No. 2010-80665
Patent Document 3: Japanese Laid-open Patent Publication No. 2008-109562

In optical coherent transmission performed by the above-described optical communication device, the following problem occurs. The receiver of the optical communication device optimizes, before AD conversion, electrical signals to be input to analog digital converters (ADCs) to be in the dynamic range of the ADCs so that an error rate in decoding the signals is reduced. When the receiver reduces the level of analog signals to be input to the ADCs for optimization, gain of clock components is reduced that are extracted from input signals in a digital signal processor arranged in the subsequent stage. A reduction in gain of clock components makes it difficult to achieve synchronization and, together with time-varying impairments and characteristics variations between lanes, it may cause decoding errors. An increase in error rate in the receiver inhibits improvement in optical transmission quality. When the receiver increases the level of the analog signals to maintain the gain of clock components, the amplitude of the analog signals exceeds the dynamic range of the ADCs. Consequently, the digital signal processor is unable to extract data components from digital signals after AD conversion.

SUMMARY

According to an aspect of the embodiments, an optical receiver receives coherent light. The optical receiver includes an amplitude adjuster, a signal processor, and a controller. The amplitude adjuster adjusts amplitude of an input signal to output an analog signal. The signal processor receives a digital signal generated from the analog signal output from the amplitude adjuster, extracts clock components from the digital signal, and after establishing synchronization between the clock components and data components, extracts the data components from the digital signal to process the data components. The controller sets amplitude of the analog signal to first amplitude before establishment of synchronization by the digital signal, and changes the set amplitude to second amplitude that is smaller than the first amplitude after the establishment of synchronization.

The object and advantages of the invention will be realized and attained by means of the elements and combinations particularly pointed out in the claims.

It is to be understood that both the foregoing general description and the following detailed description are exemplary and explanatory and are not restrictive of the invention.

DESCRIPTION OF EMBODIMENTS

Preferred embodiments will be explained with reference to accompanying drawings. The embodiment described below does not limit the scope of the optical receiver and the light receiving method disclosed in the present invention.

Figure 1:
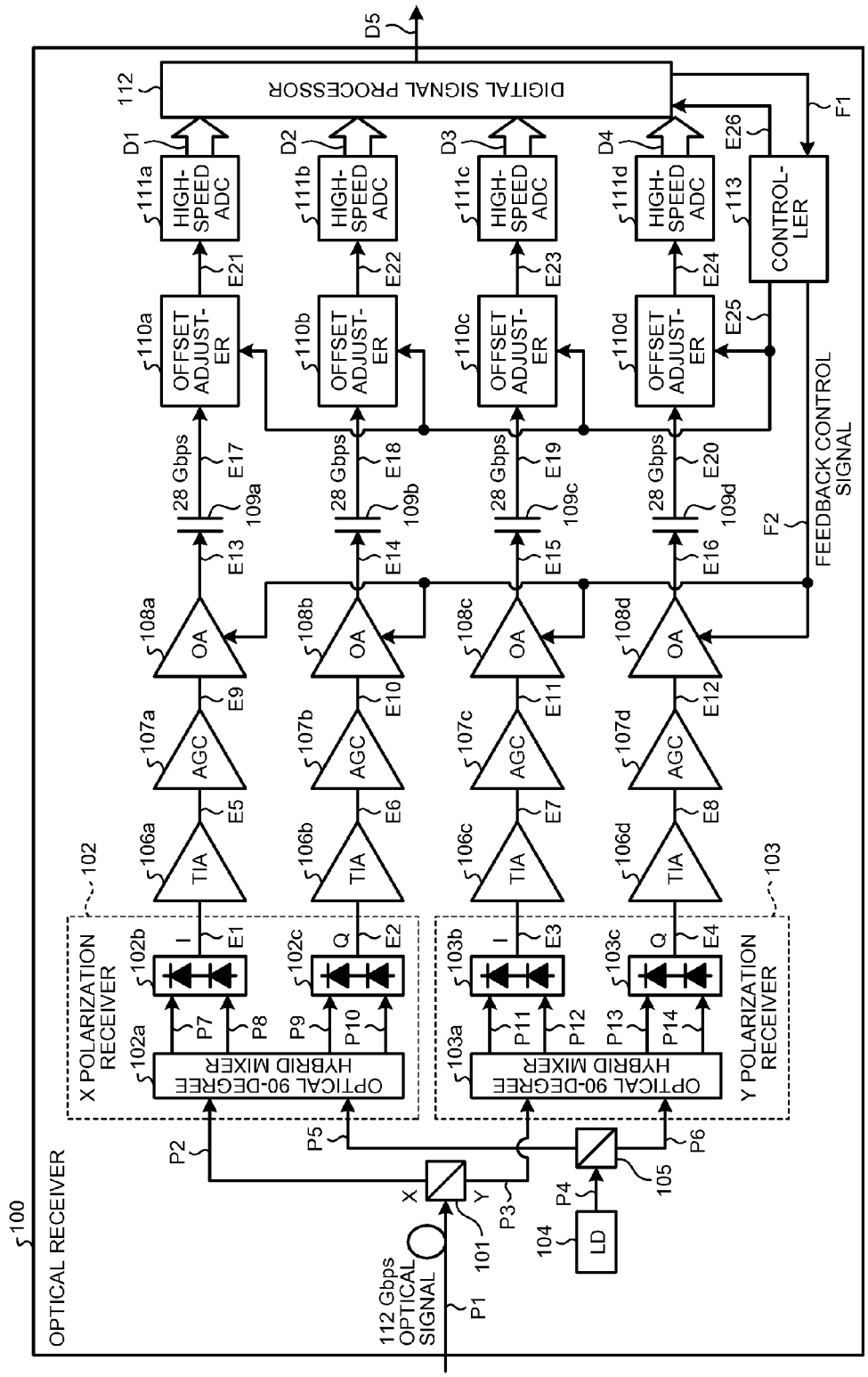
FIG. 1 is a diagram illustrating a configuration of an optical receiver according to an embodiment.

FIG. 1 is a diagram illustrating a configuration of an optical receiver 100 according to the embodiment. The optical receiver 100 and an optical transmitter (not illustrated) constitute an optical communication device using the DP-QPSK modulation scheme, for which standards are being developed by OIF. The optical transmitter translates a 100 Gbps information signal to be transmitted into four lines of 28 Gbps information signals at an error correction encoder. The four lines of information signals are input to a polarization multiplexing optical modulator. The optical transmitter includes a tunable light source that emits narrow linewidth semiconductor laser as a transmission light source. In the polarization multiplexing optical modulator, an output light beam from the transmission light source is split into two light beams, and the light beams are input to two QPSK modulators, at which each light beam is modulated into a quadrature phase shift keying light beam having a modulation rate of 28 giga symbol per second (Gsps). Signals output from the QPSK modulators are mixed by a polarization mixer, so that the signals are modulated into a polarization multiplexed signal having orthogonal polarizations (S polarization and P polarization) and output. The polarization multiplexed signal is transmitted at a transmission rate of 112 Gbps. A combined modulator may be used for a QPSK modulator that orthogonally combines input electrical signals and outputs them.

As illustrated in FIG. 1, the optical receiver 100 includes a polarization beam splitter 101, an X polarization receiver 102, a Y polarization receiver 103, a laser diode (LD) 104, a polarization beam splitter 105, trans impedance amplifiers (TIAs) 106a to 106d, and automatic gain controllers (AGCs) 107a to 107d. The optical receiver 100 includes output adjusters (OAs) 108a to 108d, capacitors 109a to 109d, offset adjusters 110a to 110d, high-speed ADCs 111a to 111d, a digital signal processor 112, and a controller 113. These components are connected such that signals and data can be input and output unidirectionally or bidirectionally.

The optical receiver 100 includes the LD 104 as a local light source that emits light having the same wavelength as that of received signal light. The optical receiver 100 performs coherent detection by mixing the received signal light with output light from the LD 104 to convert the light into an electrical signal. Coherent detection has strong polarization dependence. A single polarization receiver can only receive an optical signal in the same polarization state as that of local light. Thus, the optical receiver 100 is provided with the two polarization beam splitters 101 and 105 at a side to which a received signal is input so that the received signal is split into two orthogonal polarization components (X component and Y component). Although this configuration uses the two receivers 102 and 103 to receive one optical signal, the optical receiver 100 can compensate for degradation of the transmission rate due to a process of splitting polarization components by performing polarization multiplexing on signal light to double the volume of transmitted information.

The polarization beam splitter 101 splits a 112 Gbps optical signal P1 input thereto into two orthogonal polarization components. The X polarization receiver 102 includes an optical 90-degree hybrid mixer 102a and two balanced photodiodes 102b and 102c. The optical 90-degree hybrid mixer 102a receives a signal light beam and a local light beam (LD beam). The optical 90-degree hybrid mixer 102a mixes the received light beams in both in-phase (I) and reverse phase (Q) conditions to output a pair of output light beams P7 and P8, and mixes them in quadrature (90°, X), and reverse quadrature (−90°, Y) conditions to output a pair of output light beams P9 and P10. The optical 90-degree hybrid mixer 102a outputs a total of four light beams. The balanced photodiodes 102b and 102c arranged in the subsequent stage differentially receive the output light beams P7 and P8, and P9 and P10, respectively. This enables the balanced photodiodes 102b and 102c to eliminate unnecessary direct current (DC) components from the signal light beam and local light beam and to efficiently extract beat components of each light beam. The balanced photodiodes 102b and 102c convert the four received optical signals P7 to P10 having IQ components of X polarization and IQ components of Y polarization into electrical signals E1 and E2 (current).

The Y polarization receiver 103 includes an optical 90-degree hybrid mixer 103a and two balanced photodiodes 103b and 103c. The configuration and operation of the Y polarization receiver 103 is the same as those of the X polarization receiver 102, except that the Y polarization receiver 103 receives Y polarization components. Thus, the same constituent elements are given reference signs whose last letter is the same, and detailed description thereof is omitted.

The TIAs 106a to 106d receive electrical signals E1 to E4 output from the balanced photodiodes 102b, 102c, 103b, and 103c, respectively. In other words, the TIAs 106a and 106b receive in-phase (I) components of the received optical signals P7 and P8 and quadrature (Q) phase components of the local optical signals P9 and P10 from the respective two balanced photodiodes 102b and 102c. The TIAs 106c and 106d receive in-phase (I) components of the received optical signals P11 and P12 and quadrature (Q) phase components of the local optical signals P13 and P14 from the respective two balanced photodiodes 103b and 103c. The TIAs 106a to 106d perform impedance conversion on the input electrical signals E1 to E4 to amplify the signals, and output them as electrical signals E5 to E8.

The AGCs 107a to 107d regulate the amplitude of the electrical signals E5 to E8 received from the TIAs 106a to 106d to be an amplitude value set in advance. The OAs 108a to 108d adjust the amplitude of input signals E9 to E12 received from the AGCs 107a to 107d and output them. The OAs 108a to 108d normalize the signals by preventing degradation of signal quality lane by lane caused by differences between four lanes due to the imperfection of characteristics of analog components (the X polarization receiver 102, the Y polarization receiver 103, the TIAs 106a to 106d, the AGCs 107a to 107d, and the high-speed ADCs 111a to 111d, for example).

The capacitors 109a to 109d are passive components that electrostatically store electrical signals E13 to E16 received from the OAs 108a to 108d, respectively, and release them. The offset adjusters 110a to 110d apply bias to high-speed signals E17 to E20 from which DC components are eliminated, based on an instruction from the controller 113 such that the high-speed signals E17 to E20 are accommodated in an input range of the high-speed ADCs 111a to 111d.

Upon receiving a total of four electrical signals E21 to E24 having IQ components of X polarization and IQ components of Y polarization, the high-speed ADCs 111a to 111d perform high-speed AD conversion on these signals and outputs digital signals D1 to D4 generated by the AD conversion to the subsequent digital signal processor 112. The high-speed ADCs 111a to 111d import the analog signals E21 to E24 at a sampling frequency that is two or more times as high as that of the received signals, convert them into the digital signals D1 to D4, and output the digital signals to the digital signal processor 112.

Upon receiving the digital signals D1 to D4 from the high-speed ADCs 111a to 111d, the digital signal processor 112 performs various types of processing on the digital signals D1 to D4 based on instructions from the controller 113, corrects errors, and outputs a 100 Gbps information signal D5 to the outside of the optical receiver 100. The digital signal processor 112 performs optical frequency offset compensation, carrier phase recovery, chromatic dispersion compensation, and polarization mode dispersion compensation, for example.

The controller 113 constantly monitors the OAs 108a to 108d for adjusting amplitude and the digital signals D1 to D4 after AD conversion in each lane that transmits high-speed signals of 28 Gbps or above, and performs feedback control on the OAs 108a to 108d. In other words, the controller 113 monitors data after AD conversion by firmware processing and performs feedback control on the OAs 108a to 108d so that the amplitude of the input signals E21 to E24 are optimized within a dynamic range specific to the high-speed ADCs 111a to 111d, respectively. This enables the digital signal processor 112 to extract data components.

Figure 2:
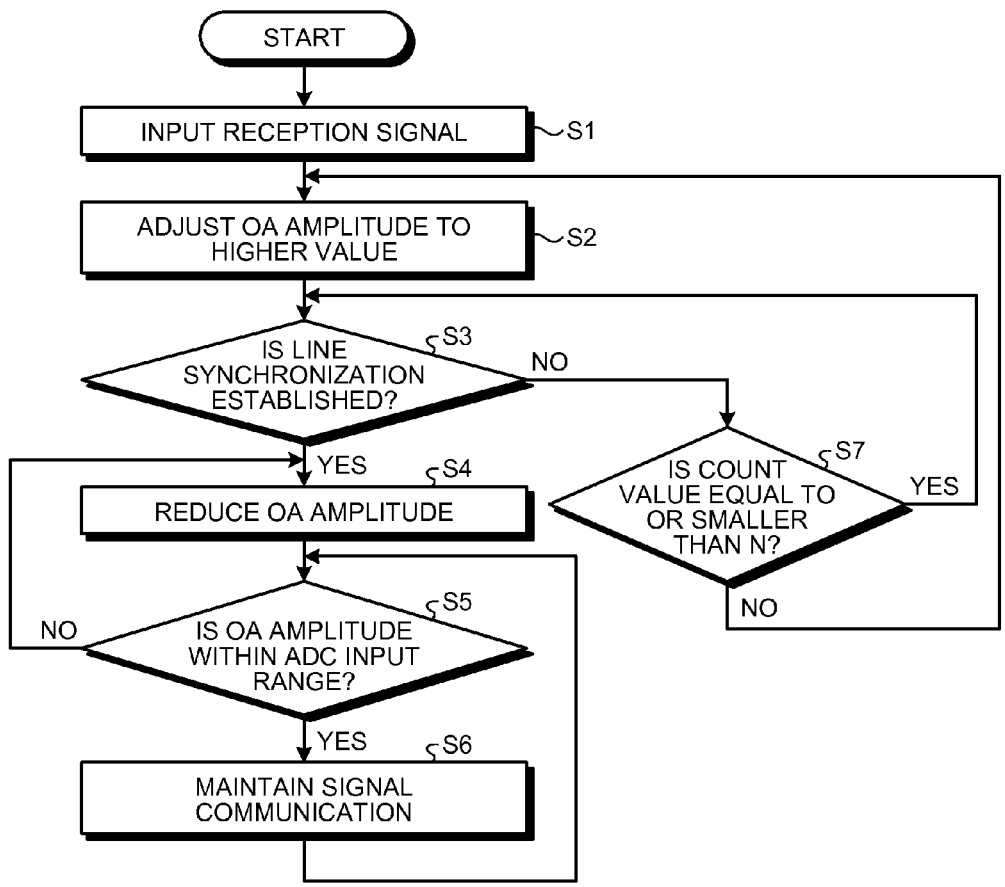
FIG. 2 is a flowchart illustrating the operation of the optical receiver according to the embodiment.

The following describes the operation of the optical receiver 100. FIG. 2 is a flowchart illustrating the operation of the optical receiver 100 according to the embodiment. On cancellation of optical power Loss Of Signal (LOS), the controller 113 of the optical receiver 100 detects an optical reception signal input to the polarization beam splitter 101 (Step S1), and adjusts signal amplitude values of the OAs 108a to 108d to higher values (Step S2). In other words, the controller 113 constantly monitors root mean square (RMS) values after AD conversion to perform feedback control so that the signal amplitude values are adjusted to the higher amplitude values set in advance. A higher amplitude value is an amplitude value with which the digital signal processor 112 can extract from the input signals D1 to D4, clock components used for establishing line synchronization, and a preferable value thereof is equal to or larger than 600 mVpp (about 700 mVpp, for example).

The controller 113 determines whether line synchronization is established at the high-speed ADCs 111a to 111d based on a feedback control signal F1 (see FIG. 1) input from the high-speed ADCs 111a to 111d via the digital signal processor 112 (Step S3). If the controller 113 determines that line synchronization is established (Yes at Step S3), it sends a feedback control signal F2 (see FIG. 1) to the OAs 108a to 108d to instruct them to lower the amplitude values that were set to higher values at Step S2 (Step S4). If each value of signal amplitude at the OAs 108a to 108d falls within an input range of the corresponding high-speed ADCs 111a to 111d (Yes at Step S5), the controller 113 determines that optimization of amplitude is completed and maintains the signal communication state (Step S6).

If any one of the signal amplitude values at the OAs 108a to 108d exceeds the input range of the corresponding high-speed ADCs 111a to 111d (No at Step S5), the process returns to Step S4, at which the controller 113 lowers the amplitude value further. The processing of lowering the amplitude values is repeated until all the signal amplitude values at the OAs 108a to 108d fall (are optimized) within the input range, and the processing ends when optimization is completed.

The controller 113 may perform the processing of lowering amplitude values for individual lanes (one lane, for example) with the amplitude value exceeding the input range, or may uniformly perform the processing for a plurality of lanes (two to four lanes, for example). The amplitude value within the input range is an amplitude value with which the digital signal processor 112 can extract subject data components from the input signals D1 to D4, and the preferable value thereof is 200 to 600 mVpp (about 300 to 500 mVpp, for example).

If line synchronization is not established after a higher amplitude value is set at Step S3 (No at Step S3), the controller 113 gradually increases the amplitude values set at Step S2 until line synchronization is established. In other words, the controller 113 holds, as a count value, an upper limit value of the number of times (ten times, for example) the controller 113 increases the amplitude values, and incrementally changes the amplitude values until the number of times (a natural number N times) reaches the count value (Step S7). If line synchronization is established (Yes at Step S3), the controller 113 starts lowering each value of the signal amplitude at the OAs 108a to 108d (Step S4). If line synchronization is not established (No at Step S3), the controller 113 increases the amplitude values (No at Step S7, Step S2) until the number of times the controller increases the amplitude values reaches the upper limit of the count value (Yes at Step S7).

When the initial setting value of amplitude at Step S2 is 600 mVpp, the controller 113 increases the amplitude value by, for example, 10 to 20 mVpp increments. The increment amount is not necessarily the same value every time the amplitude value is increased. For example, the controller 113 may increase the amplitude value by 20 mVpp each for the first five times, and may increase the amplitude value by 10 mVpp each for the following five times. The upper limit value based on which the controller 113 determines whether to increase the amplitude value to establish synchronization is not necessarily set based on the number of times (ten times, for example), but may be set based on a specific amplitude value. In this configuration, the controller 113 sets the upper limit of 800 mVpp as the above-described count value, for example, and compares the current amplitude value with this upper limit value at Step S7.

The following describes a method for extracting clock components with reference to FIGS. 3 to 7B. The following also describes why an increase in amplitude of the signals input to the digital signal processor 112 enables the optical receiver 100 to easily extract the clock components and improve characteristics to achieve synchronization.

Figure 3:
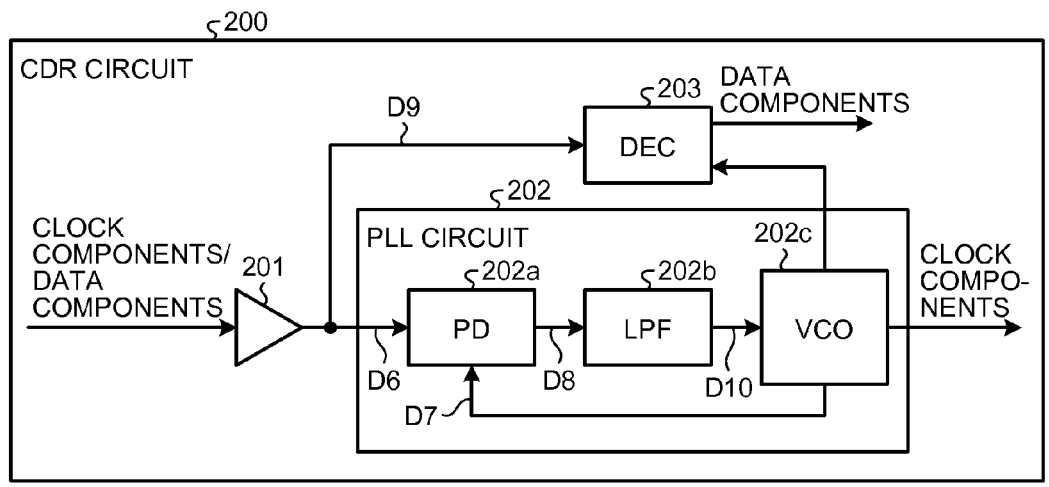
FIG. 3 is a diagram illustrating a configuration of a clock data recovery (CDR) circuit according to the embodiment.

FIG. 3 is a diagram illustrating a configuration of a clock data recovery (CDR) circuit 200 according to the embodiment. As illustrated in FIG. 3, the CDR circuit 200 includes a buffer 201, a phase locked loop (PLL) circuit 202, and a decoder 203. The PLL circuit 202 includes a phase detector (PD) 202a, a low pass filter (LPF) 202b, and a voltage controlled oscillator (VCO) 202c. These components are connected such that signals can be input and output unidirectionally or bidirectionally.

In high-speed optical transmission at about 100 Gbps, transmitted digital signals contain clock components. The CDR circuit 200 receives a digital signal transmitted in a transmission path including clock components and data components overlapped with each other, and separates the clock components and the data components in the digital signal. The CDR circuit 200 is implemented by the digital signal processor 112 of the optical receiver 100. In digital coherent communication, in particular, the CDR circuit 200 extracts clock components from, for example, four lines of serial signals that were encoded (such as forward error correction [FEC] encoding or error correction) by the optical transmitter. The clock components are used as sampling clock at the high-speed ADCs 111a to 111d.

The digital signal processor 112 of the optical receiver needs to decode both clock components and data components. As illustrated in FIG. 3, the clock components and the data components to be input to the PLL circuit 202 first pass through the buffer 201 and are bifurcated into two paths. A digital signal D6 transmitted in one path is input to the PLL circuit 202 at which clock components are extracted, and a digital signal D9 transmitted in the other path is input to the decoder 203 at which data components are generated. The phase detector 202a receives two digital signals D6 and D7 and outputs a digital signal D8 corresponding to a phase difference between these signals. The phase detector 202a, for example, generates the digital signal D8 such that the output voltage thereof is 0 V when the phase difference between the two input signals D6 and D7 is 90 degrees, and outputs the digital signal D8 to the LPF 202b in the subsequent stage.

Figure 4:
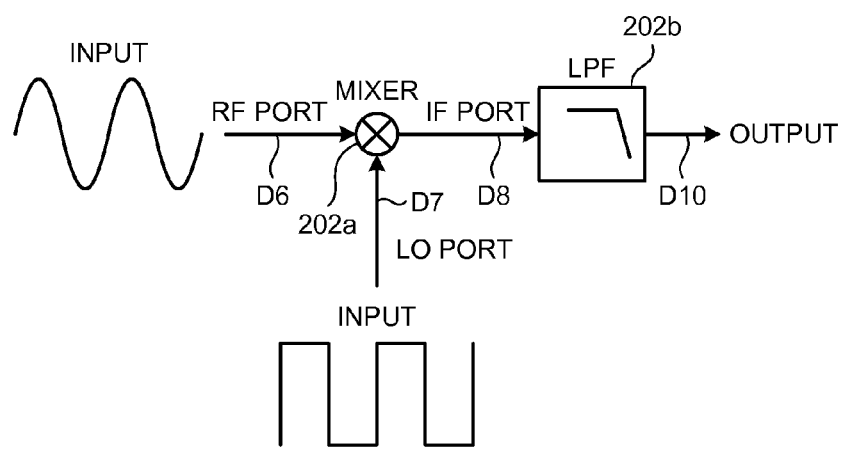
FIG. 4 is a diagram illustrating the operation of a phase detector according to the embodiment.

Next, described is the operation of the phase detector 202a by taking a mixer phase detector as an example. FIG. 4 is a diagram illustrating the operation of the phase detector 202a according to the embodiment. As illustrated in FIG. 4, the digital signal D6 having a sinusoidal waveform is input to the mixer phase detector 202a via a radio frequency (RF) port. The digital signal D7 having a rectangular waveform is input to the mixer phase detector 202a via a local oscillator (LO) port. The mixer phase detector 202a mixes the digital signals D6 and D7 having different waveforms to generate the mixer output signal D8, and the output signal D8 is input to the LPF 202b via an intermediate frequency (IF) port. The LPF 202b converts the digital signal D8 into a positive direct-current voltage and outputs it as a digital signal D10.

Figure 5A:
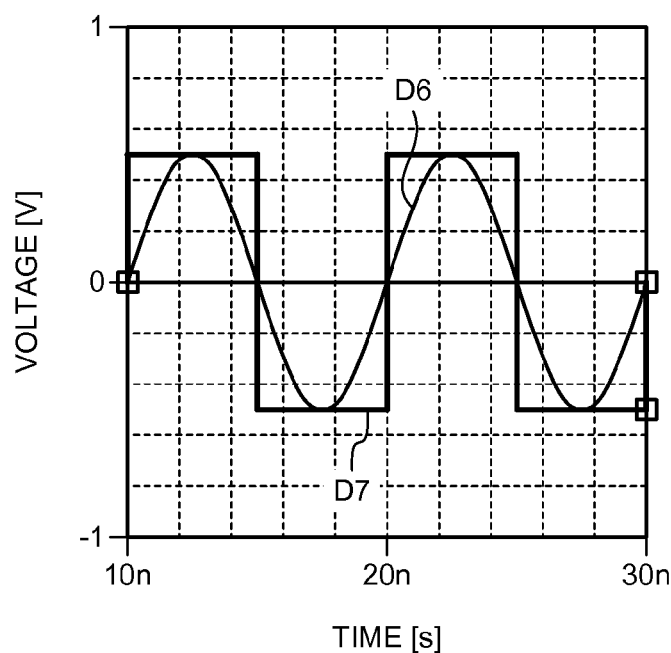
FIG. 5A is a diagram illustrating an example of waveforms of two signals input to the phase detector according to the embodiment.
Figure 5B:
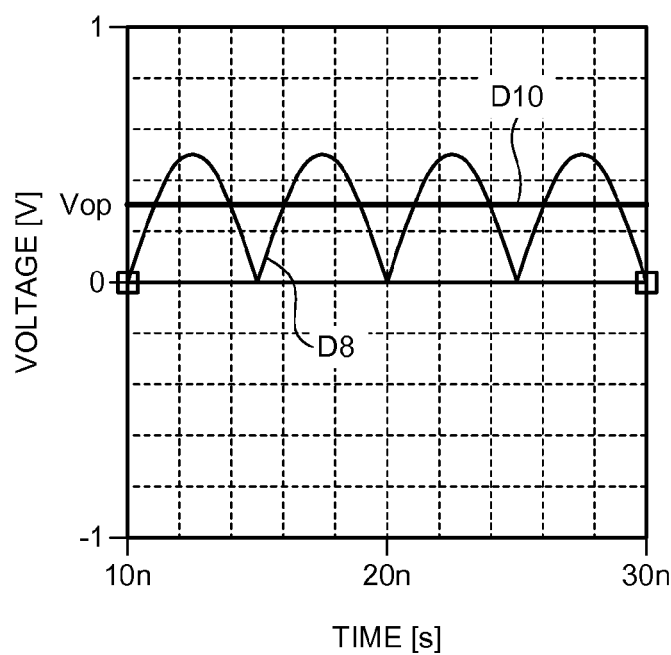
FIG. 5B is a diagram illustrating an example of a waveform of a signal output from the phase detector according to the embodiment.

FIG. 5A is a diagram illustrating an example of waveforms of two signals input to the phase detector 202a according to the embodiment. In FIG. 5A, the x-axis represents time (seconds) and the y-axis represents input signal voltage (V). As illustrated in FIG. 5A, the digital signal D6 is a sinusoidal wave having an amplitude of 0.5 V and a wavelength of 10 ns. The digital signal D7 is a rectangular wave having the same phase, amplitude, and wavelength as those of the digital signal D6. When the phase detector 202a mixes the digital signals D6 and D7, it generates a digital signal having a waveform illustrated in FIG. 5B. FIG. 5B is a diagram illustrating an example of a waveform of a signal output from the phase detector 202a according to the embodiment. As illustrated in FIG. 5B, high frequency components of the digital signal D8 are eliminated after passing through the LPF 202b, and a digital signal D10 having a positive direct-current voltage $V_{op}$ is output from the LPF 202b.

The output voltage $V_{op}$ from the LPF 202b is a control voltage for the VCO 202c. Thus, smaller amplitude of the digital signal D6 (corresponding to the digital signals D1 to D4 illustrated in FIG. 1) results in a smaller voltage $V_{op}$, that is, a smaller control voltage for the VCO 202c. This causes a decrease in clock rate that the VCO 202c can follow. At the same time, as the amplitude of the digital signal D6 decreases, the value of $T_r/T_f$ decreases (gradient becomes gentle), and the digital signal is easily affected by, for example, noise, whereby more jitter may be observed. In other words, as the amplitude of signals input to the digital signal processor 112 decreases, it becomes more difficult for the digital signal processor 112 to achieve synchronization between clock components and data components contained in the digital signals. In addition, because the digital signal D6 is transmitted at a high-speed rate of about 28 Gbps, the optical receiver 100 needs to be designed such that it corresponds to a broader frequency bandwidth. Accordingly, the optical receiver 100 increases the amplitude value of the digital signal D6 to increase the value of $T_r/T_f$ until synchronization is established. This prevents noise or other factors from affecting the digital signal and increases a clock rate that the VCO 202c can follow. Consequently, clock components can be easily extracted.

Figure 6:
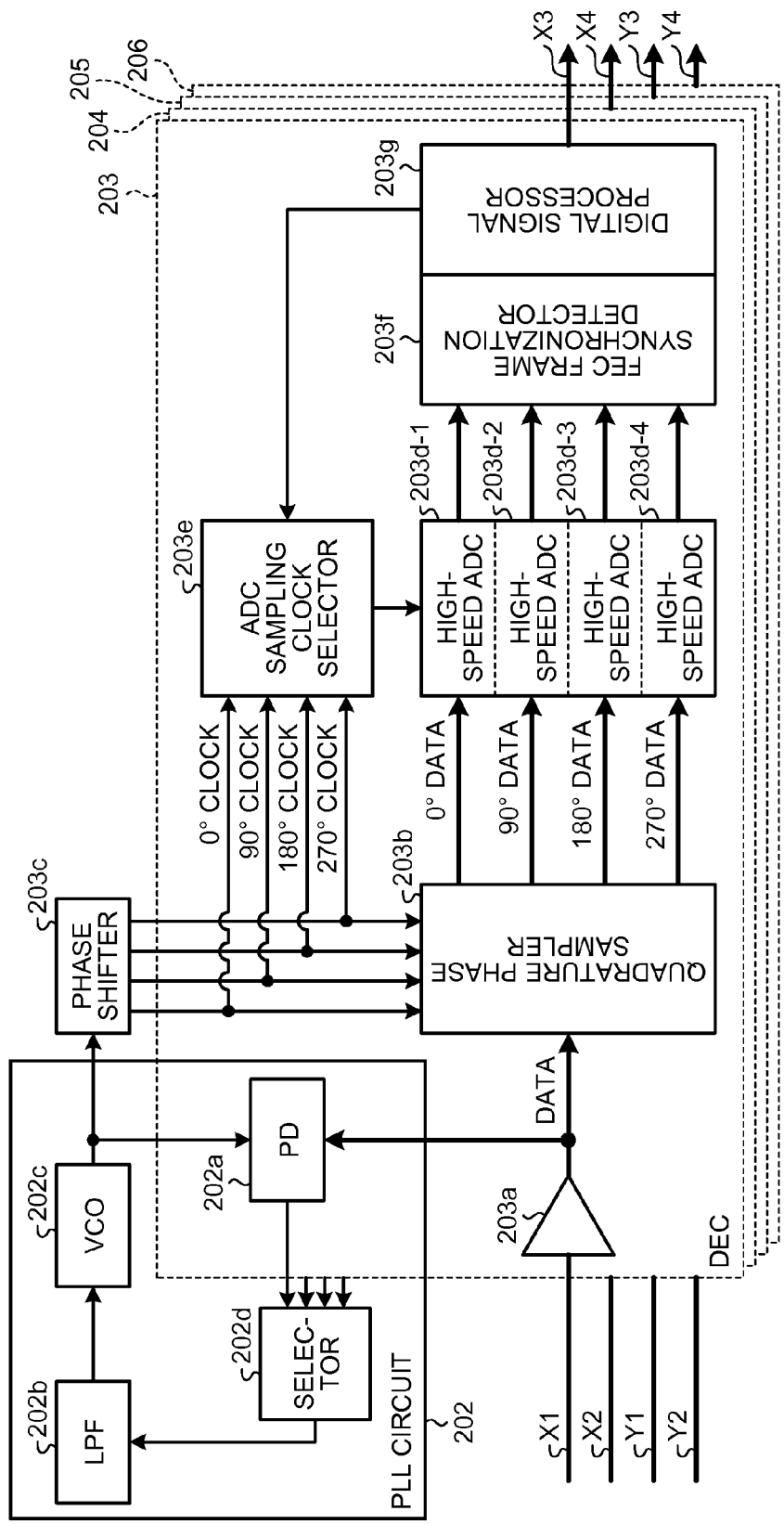
FIG. 6 is a diagram illustrating a configuration of a digital coherent receiver according to the embodiment.

FIG. 6 is a diagram illustrating a configuration of a digital coherent receiver according to the embodiment. As illustrated in FIG. 6, a phase shifter 203c shifts the phase of an output clock signal from the VCO 202c that has been synchronized with a data signal at the PLL circuit 202 into four phases (0°, 90°, 180°, and 270°). A quadrature-phase sampler 203b receives data from a buffer 203a and shifts the phase of the data into the four phases of the clock signal shifted by the phase shifter 203c. Four pieces of data having four phases shifted by the quadrature-phase sampler 203b are AD converted by high-speed ADCs 203d-1, 203d-2, 203d-3, and 203d-4, respectively, and the resulting digital signals are output to an FEC frame synchronization detector 203f. The FEC frame synchronization detector 203f detects, from the digital signals, a preamble pattern (F6 F6 F6 28 28 28) of the FEC frame.

The FEC frame synchronization detector 203f is unable to detect the FEC frame from data at a phase close to change points of data. A digital signal processor 203g arranged in the subsequent stage selects the clock closest to the middle point between the change points of data. This operation performed by the digital signal processor 203g is defined as "establishment of synchronization". With this operation, synchronization is established between clock components and data components of an XI input signal X1, an XQ input signal X2, a YI input signal Y1, and a YQ input signal Y2 that are input to decoders (DEC) 203, 204, 205, and 206, respectively. These signals are output as an XI output signal X3, an XQ output signal X4, a YI output signal Y3, and a YQ output signal Y4 to the outside of the decoders.

Figure 7A:
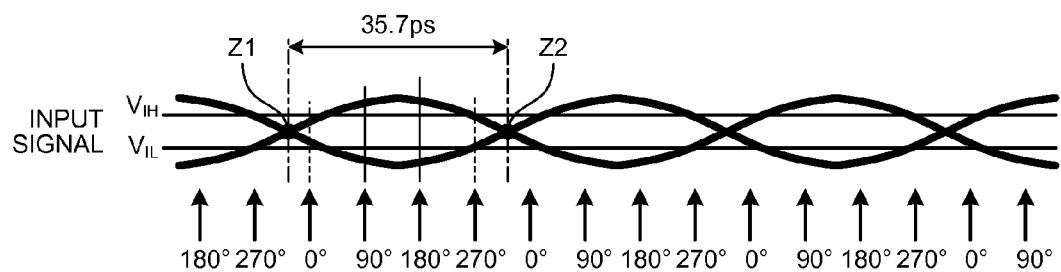
FIG. 7A is a diagram illustrating a method for establishing synchronization when input amplitude is small.
Figure 7B:
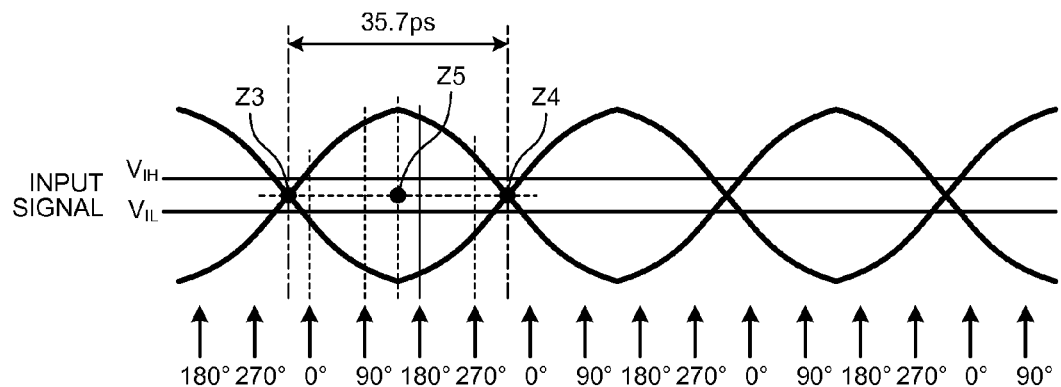
FIG. 7B is a diagram illustrating a method for establishing synchronization when input amplitude is large.

FIG. 7A is a diagram illustrating a method for establishing synchronization when input amplitude is small. FIG. 7B is a diagram illustrating a method for establishing synchronization when input amplitude is large. In FIGS. 7A and 7B, the x-axis direction (time direction) represents phase of an input signal and the y-axis direction represents voltage of the input signal. As illustrated in FIG. 7A, when input amplitude is small, the digital signal processor 203g determines that phases of 0° and 270° (indicated by the dashed lines in FIG. 7A) that are close to data change points Z1 and Z2 are phases of the data change points. The digital signal processor 203g samples either 90° or 180° (indicated by the solid lines in FIG. 7A) located between the data change points Z1 and Z2 as clock to be used for establishing synchronization. This may cause the digital signal processor 203g to fail to determine the optimal phase depending on a wavelength or frequencies of an input signal and to fail to select clock at a point most suitable for establishing synchronization.

When input amplitude is large as illustrated in FIG. 7B, the digital signal processor 203g can easily determine that the phase closest to a middle point Z5 between data change points Z3 and Z4 is 180° (indicated by the solid line in FIG. 7B). The digital signal processor 203g can, therefore, correctly select a clock phase at a point most suitable for establishing synchronization from the four phases. In other words, the digital signal processor 203g can easily and rapidly perform sampling processing for establishing synchronization. As described above, as input amplitude increases, the optical receiver 100 can more easily extract clock components from digital signals and can more easily establish synchronization.

As described above, the optical receiver 100 receives coherent light. The optical receiver 100 includes the OAs 108a to 108d, the digital signal processor 112 and the controller 113. The OAs 108a to 108d adjust amplitude of an input signal to output an analog signal. The digital signal processor 112 receives a digital signal generated from the analog signal output from the OAs 108a to 108d, extracts clock components from the digital signal, and after establishing synchronization between the clock components and data components, extracts the data components from the digital signal to process them. The controller 113 sets amplitude of the analog signal to first amplitude (larger amplitude such as about 700 mVpp) before establishment of synchronization in the digital signal. After the establishment of synchronization, the controller 113 changes the set amplitude to second amplitude (smaller amplitude such as about 400 mVpp) that is smaller than the first amplitude.

In the optical receiver 100, the first amplitude has an amplitude value equal to or larger than a value with which the digital signal processor 112 can establish synchronization between the clock components and the data components in the digital signal. The second amplitude (optimized amplitude) is within a range of amplitude with which the digital signal processor 112 can extract the data components from the digital signal. After the establishment of synchronization, the controller 113 may limit the second amplitude to amplitude within a range having linearity with respect to a gain characteristic of amplitude of output signals over control voltage applied to the OAs 108a to 108d.

In other words, the optical receiver 100 increases amplitude of electrical signals in coherent reception until synchronization is established. After the establishment of synchronization, the optical receiver 100 decreases the amplitude in accordance with the input range of the high-speed ADCs 111a to 111d. The optical receiver 100 constantly optimizes amplitude of electrical signals transmitted on respective lanes by performing feedback control after the establishment of synchronization. More specifically, the optical receiver 100 increases gain of input signals until synchronization is established to provide good stability for establishing synchronization. After synchronization is established, the optical receiver 100 performs the feedback control so that gain of the analog input signals is optimized to be in an input dynamic range by constantly monitoring digital values that have been AD converted. On adjusting gain after the establishment of synchronization, the optical receiver 100 limits the range of gain characteristics so as not to use a non-linear range in which waveform distortion may easily occur. This enables the optical receiver 100 to decrease errors in data decoding and to improve signal transmission quality.

In the present embodiment, the optical receiver 100 includes the OAs 108a to 108d and the AGCs 107a to 107d as separate units. This enables the optical receiver 100 to prevent variations between signals transmitted from the capacitors 109a to 109d to the offset adjusters 110a to 110d, and to flexibly and easily respond to changes in optical signals input to the optical receiver 100 compared with a case in which the AGCs 107a to 107d have the function of the OAs.

More specifically, in optical coherent transmission, a value of signal amplitude most suitable for extracting clock differs from a value of signal amplitude most suitable for data communication. In the conventional non return to zero (NRZ) intensity modulation scheme, the optical receiver increases amplitude of an input signal to steeply raise $T_r/T_f$, so that clock components are easily extracted and transmission line quality in data communication is improved. In the optical coherent transmission scheme, however, the optical receiver 100 sets an amplitude value output from an optical reception front end (FE) module to a lower value so that the signal amplitude falls within the input range of the high-speed ADCs 111a to 111d. In this scheme, gain of clock components extracted from input signals decreases at the digital signal processor 112 arranged in the subsequent stage. This may cause an unwanted situation such as data components and clock components fail to synchronize, or it takes a long time before establishing synchronization.

The optical receiver 100 according to the present embodiment is provided with the OAs 108a to 108d and the controller 113 to set the amplitude of input signals to the high-speed ADCs 111a to 111d to a higher value until line synchronization is established between data and clock. After the establishment of line synchronization, the optical receiver 100 optimizes the amplitude to be in an ADC dynamic range. This is effective before establishment of line synchronization in that, if input signals (sinusoidal wave) to the high-speed ADCs 111a to 111d are leveled off, the optical receiver 100 can increase gain of clock components extracted from the input signals by increasing input amplitude in establishing line synchronization at an inner PLL. This increases the probability of establishing line synchronization. After the establishment of line synchronization, the optical receiver 100 can easily extract data components.

The optical receiver 100 can perform various types of feedback control in controlling amplitude after establishment of synchronization.

For example, some conventional optical reception FE modules used in optical coherent transmission include AGC circuits. These optical reception FE modules normally depend largely upon optical input power, and thus, output amplitude is not stable in some cases. In analog components from the balanced photodiodes 102b, 102c, 103b, and 103c to the high-speed ADCs 111a to 111d, in particular, input amplitude to the high-speed ADCs 111a to 111d deviates from the optimal range due to various factors such as a change in optical input power, a change in temperature, and time-varying impairments. This may cause degradation of optical transmission quality.

To solve the disadvantage described above, the controller 113 of the optical receiver 100 may perform feedback control based on a monitoring result of the RMS value after AD conversion in controlling amplitude after establishment of synchronization. The controller 113 may also perform feedback control based on the number of errors in the input signal F1 from the digital signal processor 112. In other words, the controller 113 of the optical receiver 100 constantly monitors the RMS value or the number of errors in the digital signal processor 112 in a signal communication state after establishment of synchronization so that the amplitude of output signals E13 to E16 from the OAs 108a to 108d is always optimized to be in the ADC dynamic range. This reduces an error rate and improves signal quality. In other words, the optical receiver 100 optimizes the input amplitude to be in the dynamic range of ADC inputs after establishing line synchronization of internal clock. This prevents degradation of signals due to waveform distortion and enables the optical receiver 100 to have higher transmissivity. The optical receiver 100 monitors variations of output data characteristics due to a change in optical input power, a change in temperature, and time-varying impairments at the controller 113, and performs feedback control on the OAs 108a to 108d based on the monitoring results. This enables the optical receiver 100 to maintain the optimal input amplitude, thereby preventing degradation of optical signal quality.

In optical coherent transmission in the optical receiver 100, a total of four electrical signals corresponding to IQ components of two polarizations are transmitted in four different lanes connecting the polarization receivers 102 and 103 with the digital signal processor 112. This may cause variations of characteristics in analog components between the lanes, and the variations of characteristics may cause variations in amplitude. The variations in amplitude between lanes cause degradation of transmission quality. To prevent this, the optical receiver 100 is provided with the OAs 108a to 108d in respective lanes, so that the controller 113 can perform feedback control separately on the four lanes when controlling amplitude after establishment of synchronization. This enables the controller 113 to mitigate or eliminate the variations of characteristics and amplitude occurring between the lanes. This reduces an error rate and improves signal quality.

In other words, the optical receiver 100 separately adjusts input amplitude in the four lanes to eliminate variations occurring in the analog components between the lanes. This enables the optical receiver 100 to improve transmissivity in chromatic dispersion compensation and polarization mode dispersion compensation performed by the digital signal processor 112 arranged in the subsequent stage.

Figure 8:
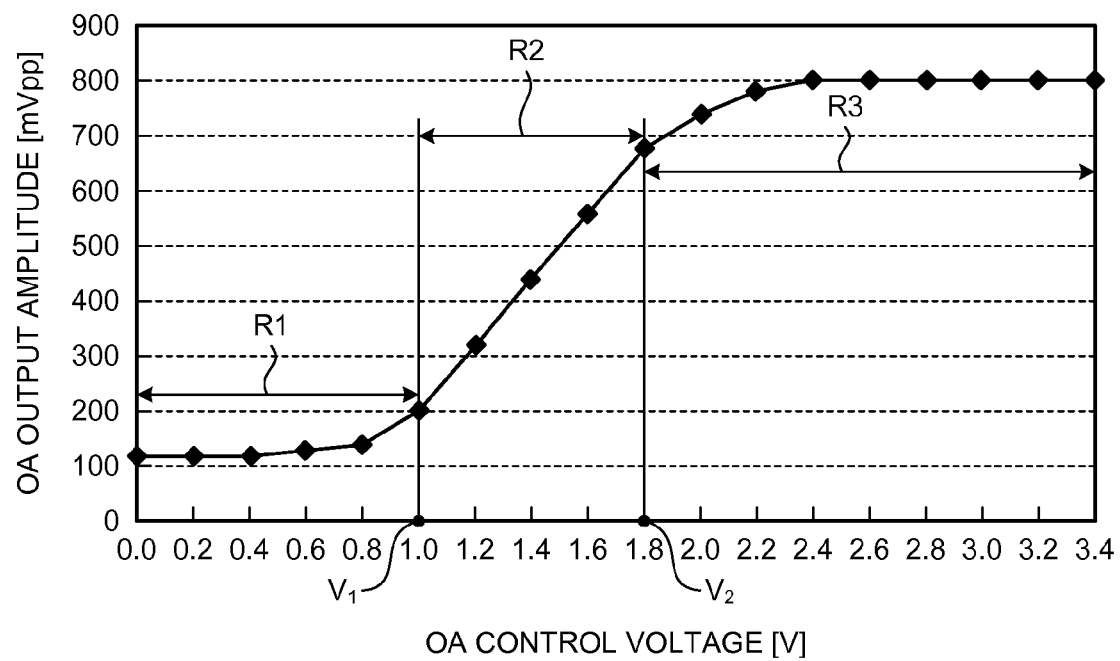
FIG. 8 is a diagram illustrating an example of a gain characteristic of an output adjuster (OA) of the optical receiver according to the embodiment.

In optical coherent transmission, maintaining good linearity is important in the analog components from the photodiodes to the ADCs. FIG. 8 is a diagram illustrating an example of a gain characteristic of the OAs 108a to 108d of the optical receiver 100 according to the present embodiment. In FIG. 8, the x-axis represents OA control voltage (V) that is voltage applied to the OAs 108a to 108d, and the y-axis represents OA output amplitude (mvpp) that is an amplitude value of an electrical signal output from the OAs 108a to 108d. As illustrated in FIG. 8, although the value of OA output amplitude increases with the OA control voltage, the increasing rate (gradient) varies depending on a value of the OA control voltage. Thus, both linear range and non-linear range appear as the OA control voltage increases.

In particular, an output level range of a high-speed operational amplifier for adjusting amplitude is predetermined, and the amplitude changes non-linearly in a range of low control voltage (such as 0 to 1.0 V) and in a range of high control voltage (such as equal to or larger than 1.8 V). FIG. 8 illustrates a non-linear range R1 in a range of low OA control voltage below $V_1$ and a non-linear range R3 in a range of high OA control voltage above $V_2$. FIG. 8 illustrates a linear range R2 (about 200 to 700 mVpp) of output amplitude in a range between the OA control voltages $V_1$ and $V_2$ (about 1.0 to 1.8 V). When the output amplitude of the high-speed ADCs 111a to 111d of the optical receiver 100 is set to a higher value (equal to or larger than 700 mVpp, for example) to establish synchronization, input signals may be clipped (saturated). When the output amplitude is set to a lower value (equal to or smaller than 200 mVpp, for example) for optimization, quantization noise is increased, thereby degrading signal quality. In other words, excessively increased amplitude causes distortion of waveform, and excessively reduced amplitude causes signals to be easily affected by noise, whereby frequency bandwidth fails to extend.

To solve the above described disadvantage, when controlling the amplitude after establishment of synchronization, the optical receiver 100 may limit the output amplitude to a value within a range in which good OA characteristics are represented (such as about 200 to 700 mVpp, more preferably, about 300 to 500 mVpp) in performing feedback control in consideration of gain of the analog components such as the OAs 108a to 108d. In other words, the controller 113 performs feedback control such that it efficiently uses the liner range R2 illustrated in FIG. 8 and a higher range (on the most significant bit [MSB] side) of the high-speed ADCs 111a to 111d in a signal communication state after the establishment of synchronization. This enables the optical receiver 100 to limit the output amplitude to a value not in the non-linear ranges of the analog components. This prevents waveform distortion and reduces an error rate. Consequently, optical signal quality is improved.

The optical receiver 100 performs the above described feedback control by firmware processing. This increases control loads of firmware. Depending on the total volume of firmware processing in the receiver, existing functions may be degraded. To prevent this, the controller 113 of the optical receiver 100 may control the amplitude after establishment of synchronization not by real-time feedback control, but by collective feedback control based on a monitoring result obtained after monitoring for a certain period (such as 1 to 100 μs) in view of stability of optical output characteristics. This reduces the volume of firmware processing performed by the controller 113, thereby reducing processing loads of the optical receiver 100.

Modification

Figure 9:
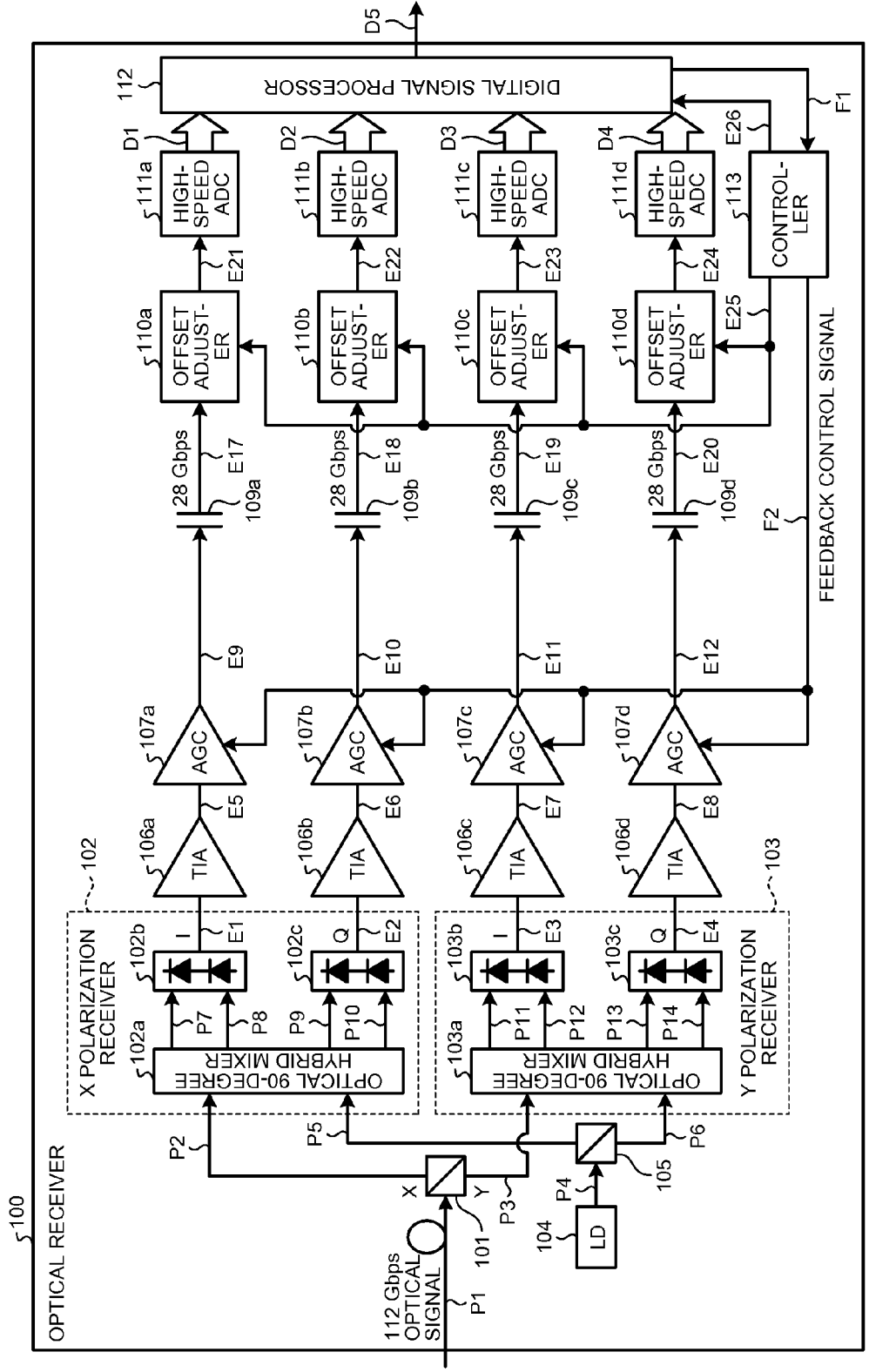
FIG. 9 is a diagram illustrating a configuration of an optical receiver according to a modification.

The above described embodiment may be modified as follows. In other words, although the OAs 108a to 108d of the optical receiver 100 are configured as independent components from the AGCs 107a to 107d in the above embodiment, the AGCs 107a to 107d may include the function of the OAs 108a to 108d. FIG. 9 is a diagram illustrating a configuration of an optical receiver 100 according to a modification. As illustrated in FIG. 9, the optical receiver 100 according to the present modification has the same configuration as that of the optical receiver 100 illustrated in FIG. 1, except that the optical receiver 100 according to the modification does not include the OAs 108a to 108d. Thus, the same reference signs are assigned to the same constituent parts, and detailed description thereof is omitted. The AGCs 107a to 107d regulates the amplitude of the electrical signals E5 to E8 input from the TIAs 106a to 106d to a preset amplitude value, and adjusts the amplitude of the electrical signals E5 to E8 and outputs the resulting electrical signals E9 to E12 to the capacitors 109a to 109d arranged in the subsequent stage. The amplitude of the electrical signals E5 to E8 is adjusted by feedback control based on the feedback control signal F2.

In the above embodiment, the feedback control is implemented with the OAs 108a to 108d that adjust amplitude provided in the four lanes of the optical receiver 100, respectively. This results in an increase in the size of the analog circuit, thereby increasing the installation footprint. In the present modification, the AGCs 107a to 107d, not the OAs 108a to 108d, adjust amplitude in the same manner as the OAs does in the feedback control performed by the optical receiver 100. This reduces the size of the analog circuit, thereby reducing the installation footprint. This enables the optical receiver 100 to have a smaller size and to reduce electric power consumption.

Although different types of methods for performing feedback control are described as separate ones, a single optical receiver 100 may use a plurality of types of methods to perform the feedback control. The number of methods of the feedback control performed by the optical receiver 100 is not limited to two, but may be equal to or larger than three, or any other form of the methods may also be used. The optical receiver 100 according to the modification is able to apply the above-described various types of methods to the feedback control. For example, the optical receiver 100 may perform feedback control individually on each of the four lanes based on the RMS value after AD conversion. The optical receiver 100 may perform collective feedback control based on the number of errors after monitoring for a predetermined period. The optical receiver 100 according to the modification may perform feedback control by limiting the amplitude of the output signals to a value within the linear range.

According to an aspect of the optical receiver disclosed in the present invention, optical transmission quality can be improved.

All examples and conditional language provided herein are intended for the pedagogical purposes of aiding the reader in understanding the invention and the concepts contributed by the inventors to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. An optical receiver that receives coherent light, the optical receiver comprising:
   an amplitude adjuster that adjusts amplitude of an input signal to output an analog signal;
   a signal processor that receives a digital signal generated from the analog signal output from the amplitude adjuster, extracts clock components from the digital signal, and after establishing synchronization between the clock components and data components, extracts the data components from the digital signal to process the data components; and
   a controller that sets amplitude of the analog signal to first amplitude before establishment of synchronization by the digital signal, and changes the set amplitude to second amplitude that is smaller than the first amplitude after the establishment of synchronization, wherein
   the controller increases gain of the input signal until synchronization is established to provide good stability for establishing synchronization, and, after synchronization is established, performs feedback control so that gain of an analog input signal is optimized to be in an input dynamic range by constantly monitoring digital values that have been analog-to-digital (AD) converted.

2. The optical receiver according to claim 1, wherein the first amplitude includes a value equal to or larger than an amplitude value with which the signal processor is able to establish synchronization between the clock components and the data components by using the digital signal.

3. The optical receiver according to claim 1, wherein the second amplitude includes a value within a range of amplitude values with which the signal processor is able to extract the data components from the digital signal.

4. The optical receiver according to claim 1, wherein the controller limits the second amplitude to amplitude within a range having linearity with respect to a gain characteristic of output amplitude over control voltage applied to the amplitude adjuster after the establishment of synchronization.

5. A light receiving method comprising:
   adjusting amplitude of an input signal to output an analog signal;
   receiving a digital signal generated from the output analog signal;
   extracting clock components from the digital signal;
   extracting, after establishing synchronization between the clock components and data components, the data components from the digital signal to process the data components;
   setting amplitude of the analog signal to first amplitude before establishment of synchronization by the digital signal;
   changing the set amplitude to second amplitude that is smaller than the first amplitude after the establishment of synchronization; and
   increasing gain of the input signal until synchronization is established to provide good stability for establishing synchronization, and, after synchronization is established, performing feedback control so that gain of an analog input signal is optimized to be in an input dynamic range by constantly monitoring digital values that have been analog-to-digital (AD) converted.

* * * * *